US00PP25787P2

(12) United States Plant Patent
Meerow

(10) Patent No.: US PP25,787 P2
(45) Date of Patent: Aug. 4, 2015

(54) ***HIPPEASTRUM* PLANT NAMED 'TAMPA'**

(50) Latin Name: ***Hippeastrum* hybrid Herb**
Varietal Denomination: Tampa

(71) Applicant: The United States of America, as represented by the Secretary of Agriculture, Washington, DC (US)

(72) Inventor: Alan W Meerow, Davie, FL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 109 days.

(21) Appl. No.: 13/998,027

(22) Filed: Sep. 24, 2013

(51) Int. Cl.
*A01H 5/02* (2006.01)

(52) U.S. Cl.
USPC ..... Plt./402

(58) Field of Classification Search
USPC ..... Plt./402
CPC ..... A01H 5/025; A01H 5/02; A01H 5/00
See application file for complete search history.

*Primary Examiner* — Kent L Bell
(74) *Attorney, Agent, or Firm* — Gail E. Poulos; John D. Fado; Lesley Shaw

(57) ABSTRACT

A new and distinct aneuploid 2n=43 semi-dwarf *Hippeastrum* hybrid plant named 'Tampa' particularly characterized by funnel-shaped flowers, measuring approximately 13-17 cm long, approximately 13-14 cm wide laterally, approximately 16-17 cm wide dorsal-ventrally, the flowers are densely striated purple approximately RHS Red Purple 60A on their inner surfaces, with a broad white RHS 155D keel.

3 Drawing Sheets

Latin name of the genus and species of the plant claimed: 'Tampa' is a new amaryllis plant that is a *Hippeastrum* Herb.

Varietal denomination: The amaryllis plant claimed is of the variety denominated 'Tampa', *Hippeastrum* hybrid Herb.

BACKGROUND OF THE INVENTION

The present invention is a new and distinct complex hybrid of *Hippeastrum* Herb., commonly known as amaryllis, a member of the family Amaryllidaceae, and is henceforth referred to by the cultivar name 'Tampa'.

'Tampa' originated as a cross made by the inventor in 2004 as part of a breeding program in Miami, Fla., USA. The objectives of the breeding program are to develop new amaryllis varieties with novel floral form and coloration and heat tolerance. The female parent is *Hippeastrum* 'Mount Blanc'× [(*H. ambiguum*×*H. papilio*)×*H.* 'Bouquet'] labeled with the breeder's code 609-04-1. The pollen parent is proprietary selection of the cross [(*Hippeastrum ambiguum*×*H. papilio*)× *H. brasilianum*]×'Wonderland' named 'Orlando' (co-pending U.S. Plant patent application Ser. No. 13/987,957).

The new cultivar was selected on the basis of its purple coloration contrasted by a broad median white stripe on the tepals. Over the course of five years of evaluation, 'Tampa' has shown excellent heat resistance, grown under ambient conditions in Miami, Fla. under 50% shade, and resistance to Red Scorch fungus (*Staganospora curtisii*).

Asexual reproduction of the new cultivar by twin-scale cuttings taken in a controlled environment in Miami, Fla. has shown that the unique features of this new amaryllis are stable and reproduced true to type in successive generations.

SUMMARY OF THE INVENTION

The following traits have been repeatedly observed and are determined to be the unique characteristics of 'Tampa'. It is contrasted with its parents in Table 1. These characteristics in combination distinguish 'Tampa' as a new and distinct cultivar:

1) The purple approximately RHS Red Purple 60A color of the tepals.
2) 'Tampa' shows resistance to Red Scorch fungus *Staganospora curtisii* and high temperatures of approximately 30-35° C., as do its parents.

TABLE 1

Comparison of *Hippeastrum* 'Tampa' and its two parent plants.

| Characteristic | 'Tampa' | Clone 609-04-1 | 'Orlando' |
|---|---|---|---|
| No. scapes per season | 3 | 2-3 | 3 |
| Scape height (cm) | 31-48 | 40-55 | 40-60 |
| No. flrs. per scape | 4-6 | 4 | 4 |
| Flr. color | Red-purple and white | Orange | Cerise pink and white |

Of the numerous commercial cultivars of amaryllis familiar to the inventor, the most similar to the new *Hippeastrum* 'Tampa' is *Hippeastrum* 'Apple Blossom' (not patented), from which 'Tampa' differs by the purple approximately RHS Red Purple 60A color of the tepals.

BRIEF DESCRIPTION OF THE PHOTOGRAPHS

DETAILED BOTANICAL DESCRIPTION

The cultivar Tampa has not been observed under all possible environmental conditions. The phenotype may vary somewhat with variations in environment such as temperature, daylength and light intensity, without, however, any variance in genotype.

Color descriptions below are based on evaluations with a Minolta CR-400 colorimeter at CIE D65/2$^0$ illumination/viewer conditions. The color parameters correspond to the uniform color space CIELAB, derived from Gonnet (Journal of Horticultural Science, Volume 68, 499-510, 1993; Food Chemistry, Volume 63, 409-415, 1998). Two color coordinates, a* and b*, as well as a psychometric index of lightness, L*, are defined. The L* is a measurement of luminosity, i.e., the equivalence of each color on the gray scale, ranging from 0 (black) to 100 (white). The a* takes positive values (0 to +60) for reddish colors and negative values (0 to −60) for the greenish ones, whereas the b* takes positive values (0 to +60) for yellowish colors and negative values (0 to −60) for the bluish ones. This is much more precise and repeatable analysis of color than obtained by using color charts (Ayala-Silva and Meerow, Proc. Intl. Trop. Hort. Soc., Volume 50, 138-144, 2006). The colorimeter takes three consecutive measurements of each sample, which was repeated three times, thus each set of color coordinates obtained are means of nine measurements. Where a reasonably close match could be discerned, The R.H.S. Colour Chart (Royal Horticultural Society, London, England, 1966) is also referenced.

TABLE 2

Colorimeter readings under the CIELAB color space for various locations on the flowers of Hippeastrum hybrid 'Tampa'. See text for explanation of the values.

Figure 1B:
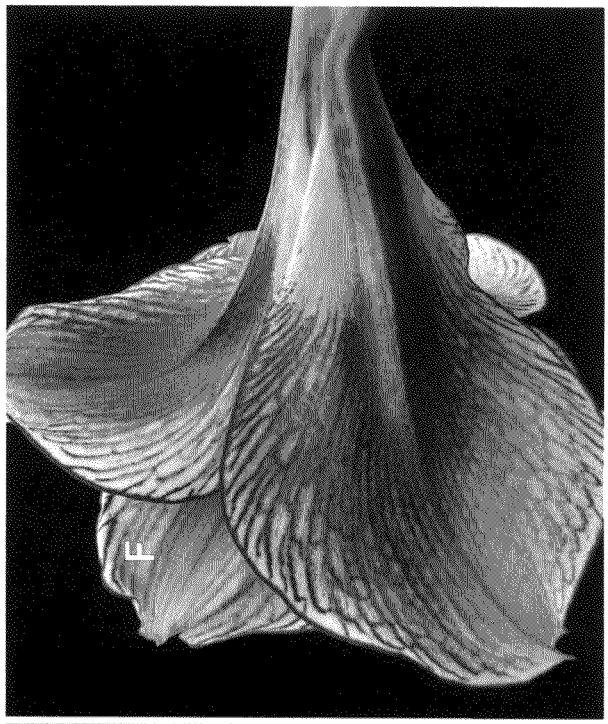
FIG. 1A and FIG. 1B are gray scale pictures of the flowers of *Hippeastrum* hybrid 'Tampa' showing the locations of colorimeter readings in Table 2.
Figure 1A:
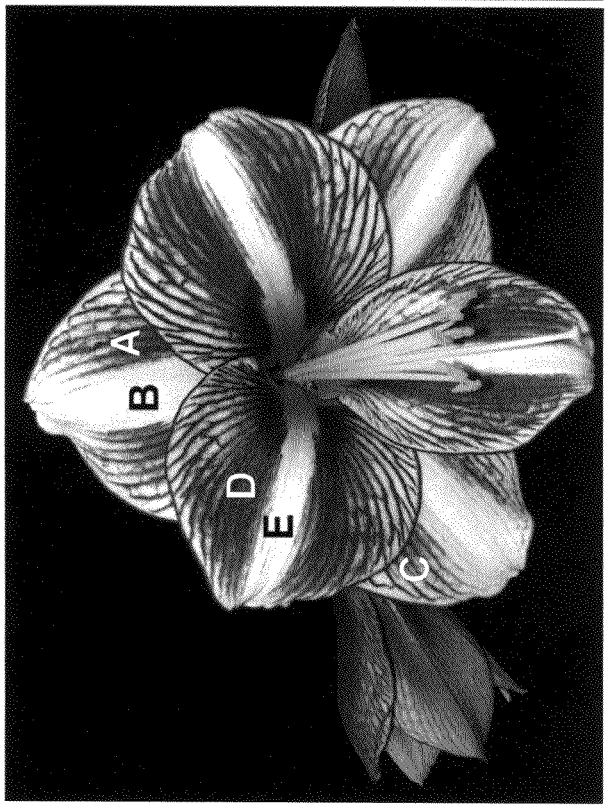
Figure 2:
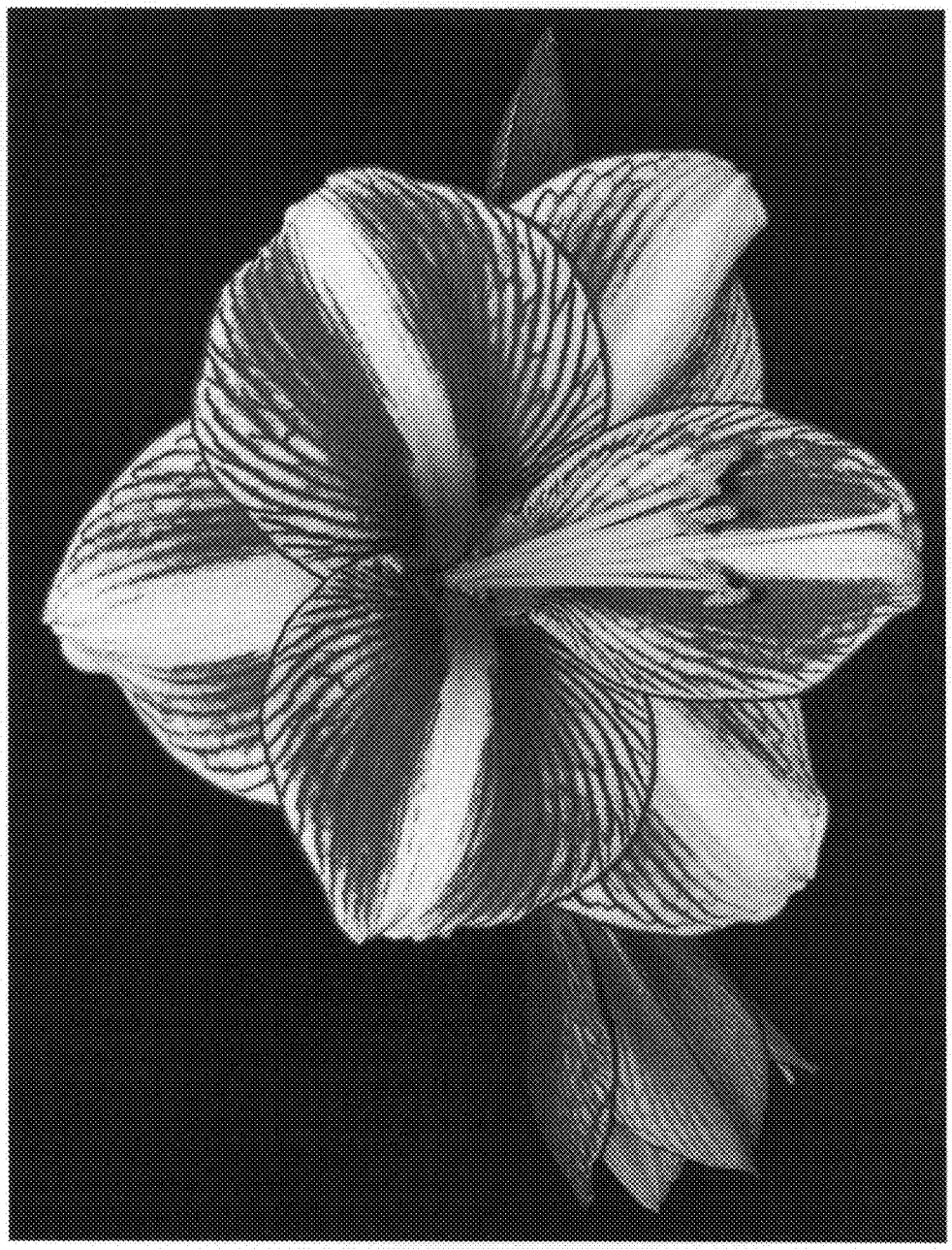
FIG. 2 and FIG. 3 are color photographs of the flower of *Hippeastrum* hybrid 'Tampa'.
Figure 3:
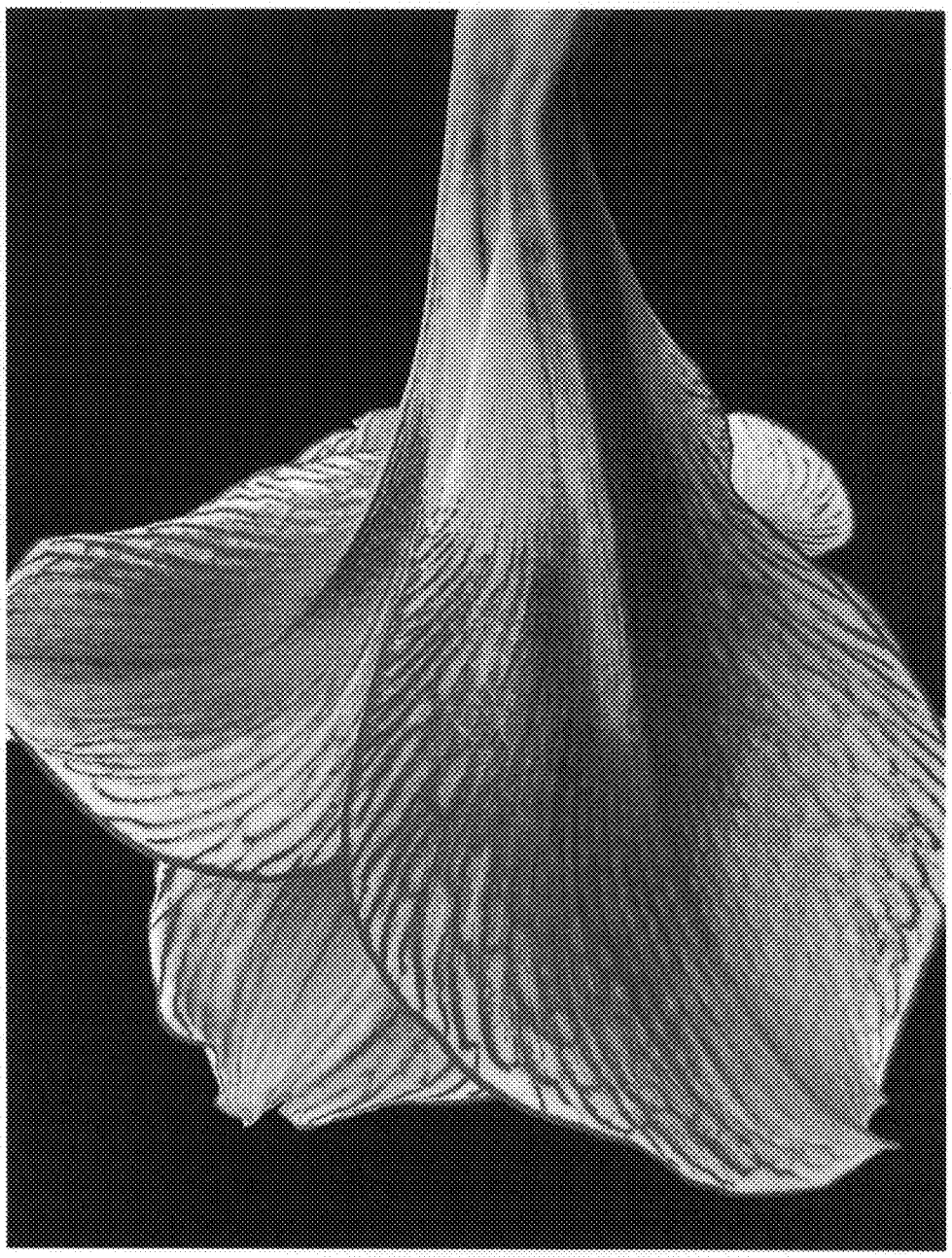

| Location (see FIG. 1) | | L*(C) | a*(C) | b*(C) |
|---|---|---|---|---|
| A | MEAN | 34.81 | 37.49 | 12.20 |
| | STDEV | 0.07 | 0.22 | 0.06 |
| B | MEAN | 80.82 | −3.21 | 10.80 |
| | STDEV | 0.09 | 0.02 | 0.04 |
| C | MEAN | 30.49 | 41.19 | 14.66 |
| | STDEV | 0.48 | 0.84 | 0.41 |
| D | MEAN | 31.25 | 37.27 | 13.13 |
| | STDEV | 1.69 | 2.19 | 0.80 |
| E | MEAN | 79.88 | −0.89 | 10.23 |
| | STDEV | 0.10 | 0.07 | 0.06 |
| F | MEAN | 31.47 | 26.77 | 11.03 |
| | STDEV | 3.77 | 6.45 | 3.29 |

Botanical classification: *Hippeastrum* hybrid cultivar Tampa.

Parentage:

*Female or seed parent.*—Proprietary selection of *Hippeastrum* 'Mount Blanc'×[(*H. ambiguum*×*H. papilio*)×*H.* 'Bouquet'] labeled with the breeder's code 609-04-1, not patented.

*Male or pollen parent.*—Proprietary selection of the cross [(*Hippeastrum ambiguum*×*H. papilio*)×*H. brasilianum*]×'Wonderland' named 'Orlando'.

Propagation:

*Type.*—Twin-scale cuttings (division of the mother bulb into vertical segments and twin-scale units).

*Time to initiate roots, summer.*—About 30 days at temperatures of approximately 30° C.

*Time to initiate roots, winter.*—About 40 days at temperatures of approximately 22° C.

*Time to develop roots, summer.*—About 65 days at temperatures of approximately 30° C.

*Time to develop roots, winter.*—About 90 days at temperatures of approximately 22° C.

Plant description:

*Appearance.*—Perennial herbaceous amaryllis. Upright and clumping growth habit, moderately dwarf.

*Crop time.*—From bulb scale cuttings, about two years are required to produce a finished, flowering plant in a 15 to 20-cm container.

*Vigor.*—Moderately vigorous.

*Plant height.*—About 60 cm.

*Plant spread.*—About 80 cm.

Roots: White RHS 155D; numerous; fine and fibrous to moderately thick and fleshy; produced from basal plate of bulb; freely branching.

Bulb:

*Diameter.*—Approximately 6-9.7 cm.

*Circumference.*—Approximately 19-30 cm.

*Shape.*—Ovoid.

*Color.*—RHS 149A; tunic, RHS 165A.

*Offsets produced per year.*—Three to five offsets per bulb.

Foliage description.

*Arrangement.*—Distichous.

*Quantity.*—6-8 per bulb.

*Length, mature leaves.*—Approximately 45-55 cm early in season, approximately 68-73 cm late in season.

*Width, mature leaves.*—About 4.5-7.0 cm.

*Shape.*—Lorate.

*Apex.*—Acute.

*Margin.*—Entire.

*Texture.*—Coarse; glabrous.

*Color.*—Young foliage, upper surface: RHS 144A.

*Young foliage, lower surface.*—RHS 144B.

*Mature foliage, upper surface.*—L*(C)=37.60, a*(C)=−13.14, b*(C)=17.66.

*Mature foliage, lower surface.*—L*(C)=43.40, a*(C)=−15.16, b*(C)=22.94.

Flower description:

*Appearance.*—Wide spreading funnel-shaped single flowers arranged in umbels borne on a leafless scape. Corolla and calyx similar (tepals), three-parted and fused at the base. Freely flowering, typically four open flowers per scape and eight to 12 flowers and flower buds per plant. Flowers last about three or four days each. Flowers persistent. Flowers held perpendicular to the scape.

*Flowering response.*—Plants flower in the spring. Plants typically flower about March 10 to April 30 in Miami, Fla.

*Fragrance.*—Not detected.

*Scape.*—Length: approximately 31-48 cm. Diameter: About 1 cm. Appearance/aspect: Leafless; upright; not fasciated, hollow. Strength: Moderate. Texture: Smooth. Color: 137D, L*(C)=46.95, a*(C)=−11.11, b*(C)=19.52.

*Pedicel.*—Approximately 5-9.5 cm long.

*Flower length.*—Approximately 13-17 cm.

*Flower diameter.*—Approximately 13-14 cm.

*Flower depth (height).*—Approximately 16-17 cm.

*Flower buds.*—Length: about 4 cm. Width: about 1 cm. Shape: Oblanceolate. Color: close to RHS Yellow-Green 144B in lower half, RHS Red Purple 60A in upper half. Rate of flower bud opening: about 2 days each, all flower opening in approximately 8-10 days.

*Tepals.*—Number: six, in two whorls of 3. Fused and forming tube in proximal 2 cm. Tube green, L*(C)=57.18, a*(C)=−14.00, b*(C)=33.41. Outer whorl: Length: approximately 12.0-12.5 cm. Width: approximately 7.5-8.0 cm. Shape: broadly ovate. Apex: apiculate. Margin: entire. Texture: Smooth;

tepals appear luminous and crystalline. Color: upper surface: striated RHS Red Purple 60A (Table 2), most intensely on laterals, green at base, with median pure white RHS 155D keels 1.3-1.5 cm wide, picotee of RHS Red Purple 60A; lower surface striations more diffuse, with white RHS 155D background, green RHS 144C towards base, keel darker, and suffused with green RHS 144C near apex and on either side in the lower ½. Inner whorl — Length of lateral: approximately 11-11.5 cm, ventral: approximately 11.5-12 cm; width of lateral: approximately 7.4-7.8 cm, ventral: approximately 6-6.5 cm. Shape: ovate, the ventral tepal narrower. Apex: apiculate. Margin: entire. Color: both surfaces: as per outer whorl (Table 2), picotee of RHS Red Purple 60A.

*Throat.*—Green (RHS 144C), with short lacinate fimbrae, and a narrow RHS Red-Purple 59B margin.

*Reproductive organs.*—Androecium: Stamen number: Six. Length: approximately 8-9 cm; filaments white RHS 155D in their distal ⅔, green RHS 144C in their proximal ⅓. Anther shape: Elliptic. Anther size: About 7 mm. Anther color: white RHS 155D. Pollen amount: Moderate. Pollen color: yellow RHS 6C. Gynoecium: Pistil number: One. Pistil length: About 11.5-12 cm. Stigma shape: tri-lobed. Stigma width: about 7 mm. Stigma color: white RHS 155D. Style color: white RHS 155D for ¾ length, green RHS 144C in lower ¼. Ovary shape: ellipsoid, ovary length: approximately 23.8-30.2 mm, ovary width: approximately 9.9-11.5 mm, ovary color: RHS 141C.

*Seed.*—Seed development has not been observed.

Chromosome number: 2n=43. Plant is aneuploid 4n−1.

Disease resistance: Plants of the new amaryllis appear resistant to Red Scorch Fungus (*Staganospora curtisii*).

Heat tolerance: Plants of the new amaryllis have demonstrated good tolerance to high temperatures about 30 to 35° C.

I claim:

1. A new and distinct cultivar of amaryllis plant genus *Hippeastrum* named 'Tampa', as illustrated and described.

* * * * *